US005614187A

United States Patent [19]

Sachs

[11] Patent Number: 5,614,187
[45] Date of Patent: Mar. 25, 1997

[54] SPECIFIC TOLERANCE IN TRANSPLANTATION

[75] Inventor: David H. Sachs, Newton, Mass.

[73] Assignees: The General Hospital Corporation, Boston, Mass.; The United States of America as represented by the Department of Health and Human Services, Washington, D.C.

[21] Appl. No.: 266,427

[22] Filed: Jun. 27, 1994

Related U.S. Application Data

[63] Continuation of Ser. No. 126,122, Sep. 23, 1993, abandoned, which is a continuation of Ser. No. 797,555, Nov. 22, 1991, abandoned.

[51] Int. Cl.$^6$ .......................... C12N 15/00; A01N 63/00; A61K 35/26; C07H 21/04
[52] U.S. Cl. ..................... 424/93.21; 424/93.3; 424/577; 536/23.1; 536/23.5; 435/172.3
[58] Field of Search ....................... 424/93.21; 435/172.3

[56] References Cited

PUBLICATIONS

PCT/US92/09849 published Jan. 7, 1993, Int. Search Report.
Pennington et al., Transplantation, vol. 45, No. 1, Issued Jan./1988, pp. 21–26.
Guzzetta et al., "Induction of Kidney Transplantation Tolerance Across Major Histocompatibility Complex Barriers by Bone Marrow Transplantation in Miniature Swine" Transplantation 51:862–866, 1991.
Lawrance et al., "Transgeneic HLA–DRa Faithfully Reconstitutes IE–Controlled Immune Functions and Induces Cross–Tolerance to Ea in Ea$^o$ Mutant Mice", Cell 58:583–594, 1989.
Sharabi et al., "Specific Tolerance Induction Across a Xenogeneic Barrier: Production of Mixed Rat/Mouse Lymphohematopoietic Chimeras Using a Nonlethal Preparative Regimen", J. Experimental Medicine 172:195–202, 1990.
Smith et al., "New approaches to Transplantation Tolerance", Transp. Proceedings 23(4):2157–2161, 1991.
Haynes et al., (1989) "The Role of Leukocyte Adhesion Molecules in Cellular Interactions: Implications for the Pathogenesis of Inflammatory Synovitis"; vol. 11, pp. 163–185.
Fischel, et al., (1991) "Prolonged Survival of a Discordant Cardiac Xenograft in a Rhesus Monkey," Transplantation Proceedings, vol. 23, No. 1, pp. 589–590, Feb. 1991.
Sachs, et al. "Human Immunology of Xenogaft Rejection" Human Immunology; vol. 28, pp. 245–251; 1990.
Wee, et al, (1992) "The Effects Of OKT4A Monoclonal Antibody on Cellular Immunity Of nonhuman primate renal allografts recipients" Transplantations, vol. 53, pp. 501–507, Mar. 1992.
Dick et al., Cell 42:71–79, 1985.
Eglitis et al., Science 230:1395–1398, 1985.
Gustafsson et al., The Journal of Immunology 145:1946–1951, 1990.

Gustafsson et al., Proc. Natl. Acad. Sci. USA 87:9798–9802, 1990.
Hirsch et al., Immunogenetics 31:52–56, 1990.
Ildstad et al., Nature 307:168–170, 1984.
Keller et al., Nature 318:149–154, 1985.
LeGuern et al., Transplantation Proceedings 23:427–428, 1991.
Lemischka et al., Cell 45:917–927, 1986.
Madsen et al., Transplantation Proceedings 21:477, 1989.
Pescovitz et al., J. Exp. Med. 160:1495–1508, 1984.
Pratt et al., Immunogenetics 31:1–6, 1990.
Sachs et al, Immunogenetics 28:22–29, 1988.
Shafer et al., Proc. Natl. Acad. Sci. USA 88:9760–9764, 1991.
Auchincloss et al., "Rejection of Transgenic Skin Expressing a Xeno–Class I Antigen is CD4–Dependent and CD8–Independent" Transpl. Proceedings 22:1059–1060 (1990).
Bach et al., "Current Concepts: Immunology" New England J. Medicine, 317:489–492 (1987).
Ilstad et al., "Characterization of Mixed Allogeneic Chimeras; Immunocompetence, In Vitro Reactivity, and Genetic Specificity of Tolerance" J. Exp. Med. 162:231–244 (1985).
Madsen,, Nature 332:161–164 (1988).
Rosengard et al., Immunology Today, 11:67–68 (1990).
Sachs, "Anti–Idiotype to MHC Receptors—A Possible Route to Specific Transplantation Tolerance", Intern. Rev. Immunol., 3:313–321 (1988).
Singer et al., "Characterization of a porcine genomic clone encoding a major histocompatibility antigen: Expression in mouse L cells" PNAS 79:1403–1407 (1982).
Sundt et al., "Applications of molecular biology to transplantation tolerance", Immunology Today, 9:342–343 (1988).
Sykes et al., "Immunobiology of Transplantation", Sykes et al., Encyclopedia. of Human Biology, 4:357–365 (1991).
LeGuern, et al., (1991) "Expression of Swine Class II Genes Using Recombinant Retroviral Vectors" *Transplantation Proceedings*, vol. 23, No. 1, pp. 427–428, Feb. 1991.
Shafer, et al., (1991) "Expression of a swine class II gene in murine bone marrow hematopoietic cells by retroviral–mediated gene transfer" *Proceeding National Academy of Science*, vol. 88, pp. 9760–9764, Nov. 1991.

(List continued on next page.)

*Primary Examiner*—Suzanne E. Ziska
*Attorney, Agent, or Firm*—Louis Myers, Esq.; Lahive & Cockfield

[57] ABSTRACT

In general, the invention features, a method of inducing tolerance in a recipient mammal, e.g., a human, of a first species to a tissue obtained from a mammal, e.g., a swine, e.g., a miniature swine, of a second species, which tissue expresses an MHC antigen, including inserting DNA encoding an MHC antigen of the second species into a bone marrow hematopoietic stem cell from the recipient mammal, and allowing the MHC antigen encoding DNA to be expressed in the recipient.

15 Claims, 4 Drawing Sheets

OTHER PUBLICATIONS

Gustafsson, et al., (1990) "Characterization and Expression of Two Allelic Class II DQB cDNA Clones" *The Journal of Immunology*, vol. 145, No. 6, pp. 1946–1951, Sep. 15, 1990.

Gustafsson, et al., (1990) "Structure of miniature swine class II DRB genes: Conservation of hypervariable amino acid residues between distantly related mammalian species" *Proceedings National Academy of Sciences*, vol. 87, pp. 9798–9802, Dec. 1990.

Hirsch, et al., (1990) "Characterization of an expressed pig class II gene Homologous to HLA–DQA" *Immunogenetics*, vol. 31, pp. 52–56.

Pratt, et al., (1990) "Molecular identification and characterization of B (β) genes from the SLA$^c$ haplotype" *Immunogenetics*, vol. 31, No. 1, pp. 1–6, 1990.

Madsen, et al., (1989) "Induction of Immunological Unresponsiveness Using Recipient Cells Transfected with Donor Class I or Class II MHC Genes" *Transplantation Proceedings*, vol. 21, No. 1, p. 477, Feb. 1989.

Pennington, et al., (1988) "Bone Marrow Transplantation in Miniature Swine" *Transplantation*, vol. 45, No. 1, pp. 21–26.

Sachs, et al., (1988) "Class II gene characterization by RFLP and by isolation from a genomic library" *Immunogenetics*, vol. 28, No. 1, pp. 22–29, 1988.

Dick, et al., (1989) "Genetic Manipulated of Hematopoietic Stem Cells with Retrovirus Vectors" *Trends in Genetics*, vol. 2, pp. 165–170.

Lemischka, et al., (1986) "Development Potential and Dynamic Behavior of Hematopoietic Stem Cells" *Cell*, vol. 45, No. 6, pp. 917–927, Jun. 20, 1986.

Dick, et al., (1985) "Introduction of a Selectable Gene into Primitive Stem Cells Capable of Long–Term Reconstruction of the Hemopoietic System of W/W$^V$ Mice" *Cell*, vol. 42, pp. 71–79.

Eglitis, et al., (1985) "Gene Expression in Mice After High Efficiency Retroviral–Mediated Gene Transfer" *Science*, vol. 230, pp. 1395–1398.

Keller, et al., (1985) "Expression of a foreign gene in myeloid and lymphoid cells derived from multipotent haematopoietic precursors" *Nature*, vol. 318, No. 6042, pp. 149–154, Nov. 14, 1985.

Ildstad, et al., (1984) "Reconstruction with syngenetic plus allogeneic or xenogeneic bone marrow leads to specific acceptance of allografts or xenografts" *Nature*, vol. 307, No. 5946, pp. 168–170, Jan. 12, 1984.

Pescovitz, et al., (1984) "Effect of Class II Antigen Matching on Renal Allograft Survival in Miniature Swine" *Journal of Experimental Medicine*, vol. 160, No. 5, pp. 1495–1508, Nov. 1984.

Stites, et al., definition of Tolerance, *In Basic and Clinical Immunology* 1984, p. 772.

Billingham, et al., (1953) "Actively Acquired Tolerance of Foreign Cells" *Nature*, vol. 172, pp. 603–606.

Billingham et al Nature 172:603, 1953.

Dick et al TIGS 2:165, 1989.

Gustoffson et al PNAS 87:9798, 1990.

Seminars in Immunology 2 401, 1990 Sykes et al.

Pescovitz JEM 160 1495, 1988.

Dick et al Trends in Genetics 2:165, 1989.

SPECIFIC TOLERANCE IN TRANSPLANTATION

This invention was made with U.S. Government support under grants from the National Institutes of Health. The government has certain rights in the invention.

This application is a continuation of application Ser. No. 08/126,122, filed on Sep. 23, 1993, now abandoned, which is a continuation of U.S. Ser. No. 07/797,555 filed Nov. 22, 1991, now abandoned.

BACKGROUND OF THE INVENTION

The invention relates to conferring tolerance to foreign tissue.

Tolerance to self major histocompatibility (MHC) antigens occurs during T cell maturation in the thymus (McDuffie et al., 1988, J. Immunol. 141:1840). It has been known since the landmark experiments of Billingham, Brent and Medawar (Billingham et al., 1953, Nat. 172:603) that exposure of the immune system to allogeneic MHC antigens during ontogeny can cause the immune system to lose reactivity to those antigens, thus leaving the animal specifically tolerant into adult life. Ever since that time, transplantation immunologists have sought means of inducing tolerance in adult animals by production of lymphohematopoietic chimeras. The induction of tolerance across MHC barriers in adult mice by whole body irradiation (WBI) and bone marrow transplantation (BMT) has been studied extensively in murine models (Rayfield et al., 1983, Transplan. 36:183; Mayumi et al., 1989, J. Exp. Med. 169:213; Sykes et al., 1988, Immunol. Today 9:23). This approach has also recently been extended to the miniature swine large animal model, in which it was demonstrated that bone marrow transplants across MHC barriers led to the induction of long-term, specific transplantation tolerance to kidney grafts from donors MHC matched to the bone marrow donors (Guzzetta et al., 1991, Transplan. 51:862).

The use of MHC mismatched BMT as a means of inducing tolerance to organ allografts is usually accompanied by several major disadvantages: the preparative regimen required for allogeneic BMT involves lethal irradiation, with its inherent risks and toxicities; clinical applicability is limited by the fact that most potential recipients do not have an appropriate MHC-matched donor, and BMT across MHC barriers causes severe graft-vs-host disease (GVHD); and removing the T lymphocytes in allogeneic bone marrow inocula (Rodt et al., 1971, Eur. J. Immunol. 4:25), to prevent GVHD is associated with increased rates of engraftment failure (Martin et al., 1988, Bone Marrow Transplant 3:445; O'Reilly et al., 1985, Transplant. Proc 17:455; Soderling et al. 1985, J. Immunol. 135:941). While these drawbacks are generally considered acceptable for the treatment of otherwise lethal malignant diseases (e.g., leukemia), they would severely limit the application of this methodology as a preparative regimen for organ transplantation, in which non-specific immunosuppressive agents, while not without major complications, are nevertheless effective.

There have been previous reports of the use of cell lines transfected with allogeneic class I and class II genes to selectively modify the immune response to subsequent tissue grafts bearing the foreign gene (Madsen et al., 1989, Transplant. Proc. 21:477). Graft prolongation by this technique was not permanent, and the mechanism is unclear. Several laboratories have demonstrated the utility of retroviral mediated gene transfer for the introduction of new genetic material into totipotent hematopoietic stem cells of mice. In general, these protocols involve the transduction of bone marrow by recombinant retroviral vectors ex vivo, with the subsequent reintroduction of the treated cells into myeloablated recipients (for review, see Dick et al., 1986, Trends in Genetics 2:165).

SUMMARY OF THE INVENTION

In general, the invention features a method of inducing tolerance in a recipient mammal, e.g., a human, of a first species to a tissue obtained from a mammal, e.g., a swine, e.g., a miniature swine, of a second species, which tissue expresses an MHC antigen, including inserting DNA encoding an MHC antigen of the second species into a bone marrow hematopoietic stem cell from the recipient mammal, and allowing the MHC antigen encoding DNA to be expressed in the recipient.

Preferred embodiments include those in which: the cell is removed from the recipient mammal prior to the DNA insertion and returned to the recipient mammal after the DNA insertion; the DNA is obtained from the individual mammal from which the tissue is obtained; the DNA is obtained from an individual mammal which is syngeneic with the individual mammal from which the tissue is obtained; the DNA is obtained from an individual mammal which is MHC matched, and preferably identical, with the individual mammal from which the tissue is obtained; the DNA includes an MHC class I gene; the DNA includes an MHC class II gene; the DNA is inserted into the cell by transduction, e.g., by a retrovirus, e.g., by a Moloney-based retrovirus; and the DNA is expressed in bone marrow cells and/or peripheral blood cells of the recipient 14, preferably 30, more preferably 60, and most preferably 120 days, after the DNA is introduced into the recipient.

In another aspect, the invention features a method of inducing tolerance in a recipient mammal, e.g., a human, to a tissue obtained from a donor mammal of the same species, which tissue expresses an MHC antigen, including: inserting DNA encoding an MHC antigen of the donor into a bone marrow hematopoietic stem cell of the recipient mammal; and allowing the MHC antigen encoding DNA to be expressed in the recipient.

Preferred embodiments include those in which: the cell is removed from the recipient prior to the DNA insertion and returned to the recipient after the DNA insertion; the DNA includes a MHC class I gene; the DNA includes a MHC class II gene; the DNA is inserted into the cell by transduction, e.g., by a retrovirus, e.g., by a Moloney-based retrovirus; and the DNA is expressed in bone marrow cells and/or peripheral blood cells of the recipient 14, preferably 30, more preferably 60, and most preferably 120 days, after the DNA is introduced into the recipient.

Tolerance, as used herein, refers to the inhibition of a graft recipient's ability to mount an immune response which would otherwise occur, e.g., in response to the introduction of a nonself MHC antigen into the recipient. Tolerance can involve humoral, cellular, or both humoral and cellular responses.

Bone marrow hematopoietic stem cell, as used herein, refers to a bone marrow cell which is capable of developing into mature myeloid and/or lymphoid cells.

MHC antigen, as used herein, refers to a protein product of one or more MHC genes; the term includes fragments or analogs of products of MHC genes which can evoke an immune response in a recipient organism. Examples of MHC antigens include the products (and fragments or analogs thereof) of the human MHC genes, i.e., the HLA genes. MHC antigens in swine, e.g., miniature swine, include the products (and fragments and analogs thereof) of the SLA genes, e.g., of the DRB gene.

Miniature swine, as used herein, refers to partially inbred miniature swine.

Graft, as used herein, refers to a body part, organ, tissue, or cells.

The invention allows the reconstitution of a graft recipient's bone marrow with transgenic autologous bone marrow cells expressing allogeneic or xenogeneic MHC genes. Expression of the transgenic MHC genes confers tolerance to grafts which exhibit the products of these or closely related MHC genes. Thus, methods of the invention provide for the induction of specific transplantation tolerance by somatic transfer of MHC genes.

Methods of the invention avoid the undesirable side effects of broad spectrum immune suppressants which are often used in transplantation. Drugs such as Prednisone, Imuran, CyA, and most recently FK506, have all had important impact on the field of transplantation. However, all of these drugs cause nonspecific suppression of the immune system which must be titrated sufficiently to avoid rejection while not completely eliminating immune function. Patients must stay on chronic immunosuppressive therapy for the remainder of their lives, facing the major complications of too much or too little immunosuppression, infection and rejection, respectively.

Tolerance to transplantation antigens can be achieved through induction of lymphohematopoietic chimerism by bone marrow transplantation (BMT). However, successful BMT across MHC barriers has two major risks: if mature T cells are not removed from the marrow inoculum the recipient may develop severe graft versus host disease (GVHD); removal of these cells often leads to failure of engraftment. Methods of the invention, which induce specific tolerance by reconstitution of the recipients bone marrow with autologous (as opposed to allogeneic or heterologous) bone marrow cells, allow tolerance to be conferred with minimal risk of GVHD and with minimal need to remove T cells from the marrow inoculum.

Other features and advantages of the invention will be apparent from the following detailed description and from the claims.

DETAILED DESCRIPTION

The drawings are first briefly described.
Drawings

MHC Genes

MHC genes for a variety of species are well studied. For example the HLA genes in man, see, e.g., Hansen et al., 1989, The Major Histocompatability Complex, In Fundamental Immunology 2d ed., W. E. Paul, ed., Raven Press Ltd., New York, hereby incorporated by reference, and the SLA genes in swine, see e.g., Sachs et al., 1988, Immunogentics 28:22–29, hereby incorporated by reference, have been cloned and characterized.

A gene encoding a MHC antigen can be used in methods of the invention to confer tolerance to a graft which displays that or a closely related MHC antigen. Methods of the invention can be used to confer tolerance to allogeneic grafts, e.g., wherein both the graft donor and the recipient are humans, and to xenogeneic grafts, e.g., wherein the graft donor is a nonhuman animal, e.g., a swine, e.g., a miniature swine, and the graft recipient is a human.

The individual which supplies the MHC genes should be as genetically similar as possible, particularly in terms of the MHC genes, to the individual which supplies the graft. For example, in allogeneic grafts wherein the implant donor is a human and the implant recipient is a human it is preferable to use MHC genes from the donor. In this embodiment, MHC probes, e.g., a probe from a third person or a synthetic consensus probe, can be used to isolate DNA encoding the MHC gene or genes of the implant donor individual. This allows the closest match between the genes used to confer tolerance and the genes which express MHC antigens on the graft.

In xenogeneic grafts, the implant donor individual and the individual which supplies the tolerance conferring DNA should be the same individual or should be as closely related as possible. For example, it is preferable to derive implant tissue from a colony of donors which is highly inbred and, more preferably, which is homozygous for the MHC genes. This allows the single cloned MHC sequence to be used for many graft recipients.

Transformation of bone marrow cells

MHC genes can be introduced into bone marrow cells by any methods which allows expression of these genes at a level and for a period sufficient to confer tolerance. These methods include e.g., transfection, electoporation, particle gun bombardment, and transduction by viral vectors, e.g., by retroviruses.

Recombinant retroviruses are a preferred delivery system. They have been developed extensively over the past few years as vehicles for gene transfer, see e.g., Eglitis et al., 1988, Adv. Exp. Med. Biol. 241:19. The most straightforward retroviral vector construct is one in which the structural genes of the virus are replaced by a single gene which is then transcribed under the control of regulatory elements contained in the viral long terminal repeat (LTR). A variety of single-gene-vector backbones have been used, including the Moloney murine leukemia virus (MoMuLV). Retroviral vectors which permit multiple insertions of different genes such as a gene for a selectable marker and a second gene of interest, under the control of an internal promoter can be derived from this type of backbone, see e.g., Gilboa, 1988, Adv. Exp. Med. Biol. 241:29.

The elements of the construction of vectors for the expression of a protein product, e.g., the choice of promoters is known to those skilled in the art. The most efficient expression from retroviral vectors is observed when "strong' promoters are used to control transcription, such as the SV 40 promoter or LTR promoters, reviewed in Chang et al., 1989, Int. J. Cell Cloning 7:264. These promoters are constitutive and do not generally permit tissue-specific expression. However, in the case of class I genes, which are normally expressed in all tissues, ubiquitous expression is acceptable for functional purposes. Housekeeping gene promoters, e.g., the thymidine kinase promoter, are appropriate promoters for the expression of class II genes.

The use of efficient packaging cell lines can increase both the efficiency and the spectrum of infectivity of the produced recombinant virions, see Miller, 1990, Human Gene Therapy 1:5. Murine retroviral vectors have been useful for transferring genes efficiently into murine embryonic, see e.g., Wagner et al., 1985, EMBO J. 4:663; Griedley et al., 1987 Trends Genet. 3:162, and hematopoietic stem cells, see e.g., Lemischka et al., 1986, Cell 45:917–927; Dick et al., 1986, Trends in Genetics 2:165–170.

A recent improvement in retroviral technology which permits attainment of much higher viral titers than were previously possible involves amplification by consecutive transfer between ecotropic and amphotropic packaging cell lines, the so-called "ping-pong" method, see e.g., Kozak et al., 1990, J. Virol. 64:3500–3508; Bodine et al., 1989, Prog. Clin. Biol. Res. 319:589–600.

Transduction efficiencies can be enhanced by preselection of infected marrow prior to introduction into recipients, enriching for those bone marrow cells expressing high levels of the selectable gene, see e.g., Dick et al., 1985, Cell 42:71–79; Keller et al., 1985, Nature 318:149–154. In addition, recent techniques for increasing viral titers permit the use of virus-containing supernatants rather than direct incubation with virus-producing cell lines to attain efficient transduction, see e.g., Bodine et al., 1989, Prog. Clin. Biol. Res. 319:589–600. Because replication of cellular DNA is required for integration of retroviral vectors into the host genome, it may be desirable to increase the frequency at which target stem cells which are actively cycling e.g., by inducing target cells to divide by treatment in vitro with growth factors, see e.g., Lemischka et al., 1986, Cell 45:917–927, a combination of IL-3 and IL-6 apparently being the most efficacious, see e.g., Bodine et al., 1989, Proc. Natl. Acad. Sci. 86:8897–8901, or to expose the recipient to 5-fluorouracil, see e.g., Mori et al., 1984, Jpn. J. Clin. Oncol. 14 Suppl 1:457–463, prior to marrow harvest, see e.g., Lemischka et al., 1986, Cell 45:917–927; Chang et al., 1989, Int. J. Cell Cloning 7:264–280.

N2A or other Moloney-based vectors are preferred retroviral vectors for transducing human bone marrow cells.

Preparative Regimen For The Introduction of Transformed Bone Marrow Cells

To prepare for bone marrow cells the recipient must undergo an ablation of the immune response which might otherwise resist engraftment.

The preparative regimens necessary to permit engraftment of modified autologous hematopoietic stem cells may be much less toxic than those needed for allogeneic bone marrow transplantation—preferably requiring only depletion of mature T cells with monoclonal antibodies, as has been recently demonstrated in a mouse model, see Sharabi et al., 1989, J. Exp. Med. 169:493–502. It is possible that transient expression may be sufficient to induce tolerance, which may then be maintained by the transplant even if expression on hematopoietic cells is lost, as has been observed for heart transplants in a mixed xenogeneic bone marrow transplant model, Ildstad et al., 1985, Transplant. Proc. 17:535–538.

EXAMPLE 1

Sustained expression of a swine class II gene in murine bone marrow hematopoietic cells by retroviral-mediated gene transfer Overview The efficacy of a gene transfer approach to the induction of transplantation tolerance in miniature swine model was shown by using double-copy retroviral vectors engineered to express a drug-resistance marker (neomycin) and a swine class II DRB cDNA. Infectious particles containing these vectors were produced at a titer of >1×10$^6$ G418-resistant colony-forming units/ml using both ecotropic and amphotropic packaging cell lines. Flow cytometric analysis of DRA-transfected murine fibroblasts subsequently transduced with virus-containing supernatants demonstrated that the transferred sequences were sufficient to produce DR surface expression. Cocultivation of murine bone marrow with high-titer producer lines leads to the transduction of 40% of granulocyte/macrophage colony-forming units (CFU-GM) as determined by the frequency of colony formation under G418 selection. After nearly 5 weeks in long-term bone marrow culture, virus-exposed marrow still contained G418-resistant CFU-GM at a frequency of 25%. In addition, virtually all of the transduced and selected colonies contained DRB-specific transcripts. These results show that a significant proportion of very primitive myelopoietic precursor cells can be transduced with the DRB recombinant vector and that vector sequences are expressed in the differentiated progeny of these cells. These experiments are described in detail below.

Construction and Screening of SLA-DRB Recombinant Retroviruses As in man, Lee et al., 1982, Nature 299:750–752, Das et al., 1983, Proc. Natl. Acad. Sci. USA 80:3543–3547, the sequence of the swine DRA gene is minimally polymorphic. Therefore, transduction of allogeneic DRB cDNAs into bone marrow cells should be sufficient to allow expression of allogeneic class II DR molecules on cells committed to express this antigen.

Figure 1:
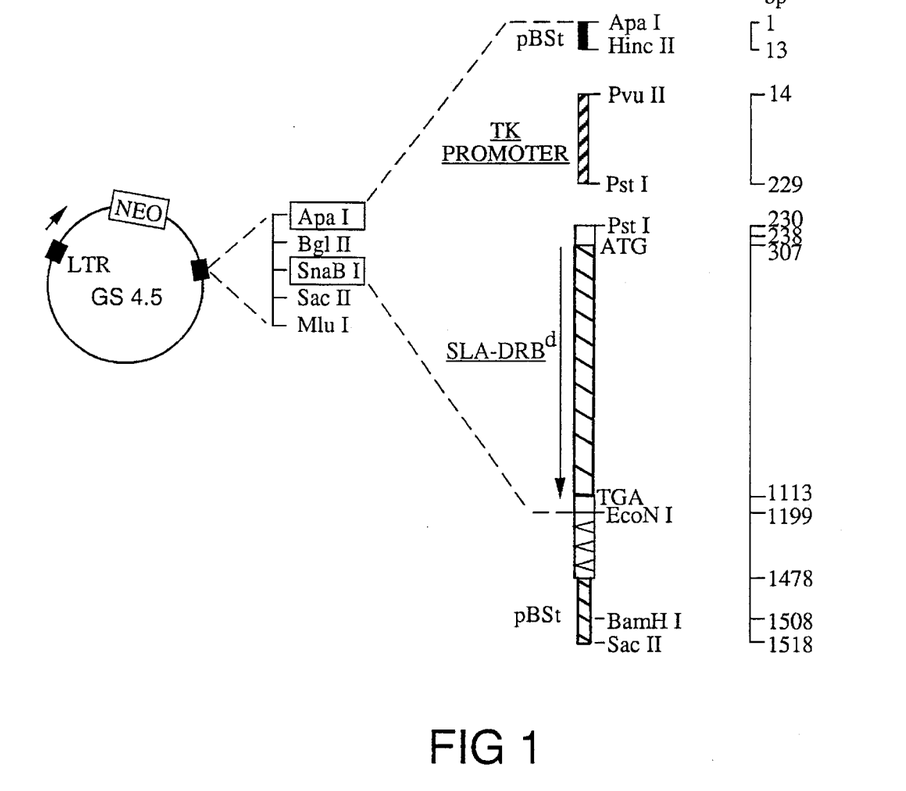
FIG. 1 is a diagram of the GS4.5 retroviral construct.

Details of retroviral constructs are given in FIG. 1. Two types of retroviral constructs, GS4.4 and GS4.5, were prepared. The diagram in FIG. 1 depicts the GS4.5 retroviral construct. The arrows in FIG. 1 indicate the directions of transcription. In GS4.5, the orientation of DRB cDNA transcription is the same as viral transcription. In GS4.4 (not shown), the TK promoter and the DRB cDNA were inserted into the 3' LTR of N2A in the reverse orientation of transcription with respect to viral transcription and the simian virus 40 3' RNA processing signal was added. pBSt refers to Bluescript vector sequence (Stratagene). The thymidine kinase (TK) promoter was contained within the 215-base-pair (bp) Pvu II-Pst I fragment from the herpes simplex virus TK gene, McKnight, 1980 Nucleic Acids Res. 15:5949–5964. The simian virus 40 3' RNA processing signal was contained within the 142-bp Hpa I-Sma I fragment from the pBLCAT3 plasmid, Luckow et al., (1987) Nucleic Acids Res. 15:5490–5497, (see FIG. 1). Sequence analysis of the junctions of the promoter, the class II cDNA, and the vector sequences confirmed that the elements of the constructs were properly ligated.

These retroviral constructs were transfected into the amphotropic packaging cell line PA317, and transfectants were selected in G418-containing medium. A total of 24 and 36 clones, transfected, respectively, with the GS4.4 and GS4.5 recombinant plasmids, were tested by PEG precipitation of culture supernatants and slot-blot analysis of viral RNA. Of these, 8 and 12 clones were found, respectively, to be positive for DRB, although the DRB signal was consistently weaker for the GS4.4-derived clones. Analysis of genomic and spliced transcripts from GS4.5 cells by dot-blot analysis of PEG-precipitated particles revealed heterogeneity among viral transcripts in various clones transfected by GS4.5. In one experiment, two clones contained DRB$^+$/Neo$^+$ viral RNA, two contained DRB$^+$/Neo$^-$ RNA, two contained DRB$^-$/Neo$^+$ RNA, and one showed no class II or Neo signal. G418-resistance (G418$^r$) titer determination of supernatants from DRB-positive clones confirmed that the average titer produced by GS4.5-transfected clones ($10^3$–$10^4$ CFU/ml) was significantly higher than that of the GS4.4-transfected clones ($10^2$–$10^3$ CFU/ml). Further transduction experiments were, therefore, conducted with the best clone, named GS4.5 C4, which produced an initial G418$^r$ titer of $3\times10^4$ CFU/ml.

Plasmid preparation, cloning procedures, DNA sequencing, RNA preparations, Northern blots, and RNA slot blots were performed by standard methods, Sambrook et al., 1989, Molecular Cloning: A Laboratory Manual 2nd Ed. (Cold Spring Harbor Lab., Cold Spring Harbor). Final washes of blots were carried out in 0.1×SSPE (1×SSPE= 0.18M NaCl/10 mM sodium phosphate, pH 7.4/1 mM EDTA) at 60° C. for 30 min.

The packaging cell lines PA317, Miller et al., 1986, Mol. Cell. Biol. 6:2895–2902, GP+E-86, Markowitz et al., 1988, J. Virol 62:1120–1124, psiCRIP, Danos et al., 1988, Proc. Natl. Acad. Sci. USA 85:6460–6464, and their derivatives were maintained at 37° C. in Dulbecco's modified Eagle's medium (DMEM; GIBCO) with 10% (vol/vol) fetal bovine serum (CELLect Silver; Flow Laboratories) supplemented with 0.1 mM nonessential amino acids (Whittaker Bioproducts), antibiotics penicillin (5 units/ml), and streptomycin (5 μg/ml).

Improvement of the Viral Titer of the C4 Clone Since recent data indicated that supernatants containing high retroviral titers were the best candidates for transducing bone marrow cells, Bodine et al., 1990, Proc. Natl. Acad. Sci. USA 87:3738–3742, the titer of the C4 producer clone was increased by "ping-pong" amplification, Bestwick et al., 1988, Proc. Natl. Acad. Sci. USA 8.5:5404–5408. Supernatant from nearly confluent C4 cultures was used to transduce GP+E-86 ecotropic packaging cells and G418 selection was applied. Forty-eight clones were isolated and screened by PEG precipitation for production of viral particles. Supernatants from 18 of these clones were DRB-positive by dot-blot analysis of viral RNA and had G418$^r$ titers between 0.5 and $3.5\times10^4$ CFU/ml). One positive clone was then amplified by the ping-pong technique with the amphotropic hygromycin-resistant packaging line psiCRIP. Supernatants from 48 hygromycin-resistant clones were examined for presence of DRB-positive viral RNA by PEG precipitation and their G418$^r$ titers were determined. All of the clones were positive by dot-blot analysis with the DRB probes and produced titers between $1\times10^5$ and $1\times10^7$ CFU/ml. Amphotropic clone GS4.5-A4, which produced the highest titer, was tested for the presence of helper virus by the S+L-assay. No replication-competent helper virus was detected.

Amplification of virus titer was achieved by the ping-pong technique. Since there is evidence that psiCRIP packaging cells are less prone to produce helper virus than PA317 when using certain types of vectors, Miller, 1990, Hum. Gene Therapy 1:5–14, DRB recombinant virions were prepared using the psiCRIP/GP-E-86 producer combination. Titer values>$1\times10^7$ CFU/ml with no detectable amphotropic helper viruses were obtained, confirming that this strategy produced safe viral particles suitable for in vivo experiments.

Northern blot analysis of GS4.5-producing clones C4, A9, and A4, each derived form a different packaging cell line, showed a conserved hybridization pattern. RNA species corresponding to the full-length viral genome, the spliced Neo transcript, and the DRB transcription unit were observed with additional RNA species. High molecular size species observed in these experiments may constitute a read-through transcript starting from the TK promoter and ending in the other long terminal repeat (LTR). In contrast to many of the virion-producer clones obtained by transfection that presented erratic DRB transcripts, those obtained by transduction showed stable DRB hybridization patterns suggesting that no recombination events occurred during the amplification procedure.

Retroviral titers were determined as follows. Replication-defective retroviral particles were produced from packaging cell lines initially transfected with recombinant construct using the standard calcium phosphate precipitation method, Wigler et al., 1978, Cell 14:725–733. Retrovirus production was estimated by the drug-resistance titer (G418-resistant colony-forming units/ml, CFU/ml) as described, Bodine et al., 1990, Proc. Natl. Acad. Sci. USA 87:3738–3742. Except for the psiCRIP line, G418 (GIBCO) selection was carried out in active component at 500 μg/ml for 10–12 days. Hygromycin B selection was applied to psiCRIP-derived packaging clones in medium containing active drug at 50 μg/ml for 10 days. Replication-competent helper virus titer was assayed on PG4 feline cells by the S$^+$L$^-$ method, Bassen et al., 1971, Nature 229:564–566.

PEG precipitation of viral particles was performed as follows. Virions contained in 1 ml of culture supernatant were precipitated with 0.5 ml of 30% (wt/vol) polyethylene glycol (PEG) for 30 min. at 4° C. After centrifugation, the pellets were treated with a mixture of RNase inhibitors (vanadyl ribonuclease complex, BRL), phenol/chloroform-extracted, and ethanol-precipitated. Pellets were then resuspended in 15.7% (vol/vol) formaldehyde and serial dilutions were dotted onto nitrocellulose membrane.

Figure 2:
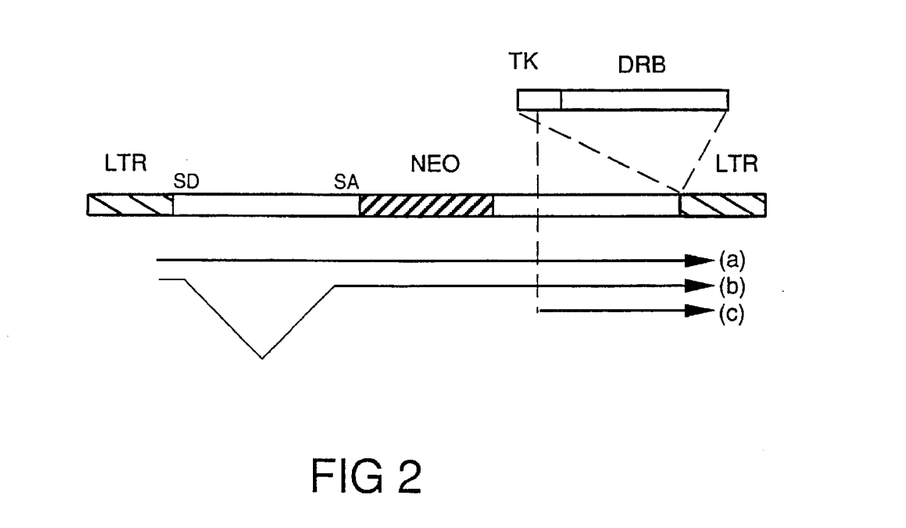
FIG. 2 is a diagram of the GS4.5 proviral genome and the expected transcripts.

Analysis of DRB Transcription in Packaging Cell Clones To test for accurate transcription of the introduced DRB cDNA within the different producer clones, Northern blots containing RNAs isolated from these clones were hybridized with the DRB and Neo probes. FIG. 2 depicts the structure of the provirus genome and the expected sizes of transcripts initiated from either the viral LTR or the TK promoters. Each of the three GS4.5-containing clones, which were derived from PA317 (clone C4), GP+E-86 (clone A9), and psiCRIP (clone A4) cells, showed DRB-positive transcripts. As reported, Hantzopoulos et al., 1989, Proc. Natl. Acad. Sci. USA 86:3519–3523, the unspliced genomic RNA (band a) and the spliced Neo transcript (band b) were observed. In addition, a transcript uniquely hybridizable with the DRB probe was detected that corresponds to the size predicted (1700 bases, band c) for the DRB cDNA transcription unit.

Figure 3A:
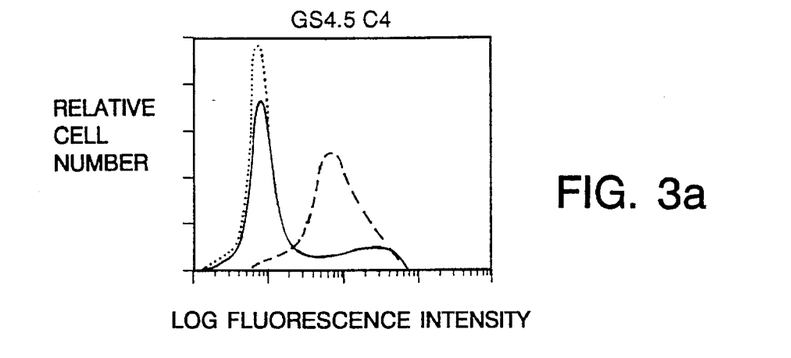
FIG. 3 is a representation of flow cytometry profile of tranduced cells.
Figure 3B:
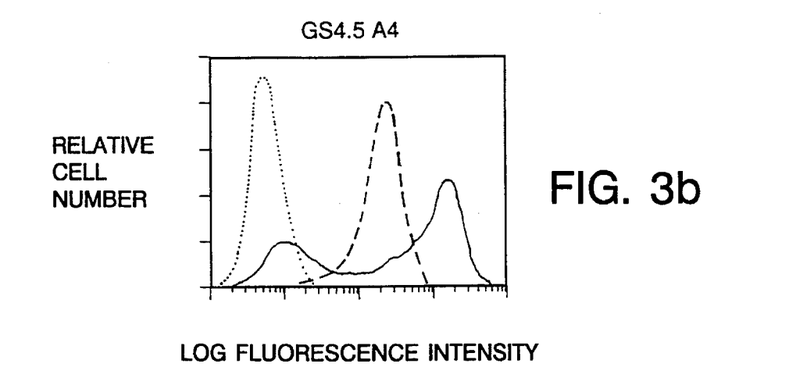

Surface Expression of the SLA-DR Antigen on Transduced Fibroblasts An in vitro assay was developed to examine surface expression of the SLA-DR antigen on murine fibroblasts. Flow cytometry (FCM) profiles shown in FIG. 3 demonstrate that G418$^r$ titers of $3\times10^4$ (clone C4) were sufficient to promote expression of the DR antigen on the cell surface of transduced DRA transfectants. In FIG. 3 solid lines indicate DR cell surface expression (anti-DR antibody binding) (22% and 75% of the bulk population of cells 3 days after transduction with GS4.5 C4, (B) and GS4.5 A4 (C), respectively); dashed lines indicate anti-mouse class I antibody binding (positive control); dotted lines indicate anti-pig CD8 antibody binding (negative control). Twenty-two percent of the bulk population of transduced cells were DR-positive and subclones maintained class II expression for more than 5 months. The increase in titer (clone A4) correlated with an increase in the number of cells transduced (75% of the transduced population was DR-positive) and with the brightness of the DR signal.

Figure 4:
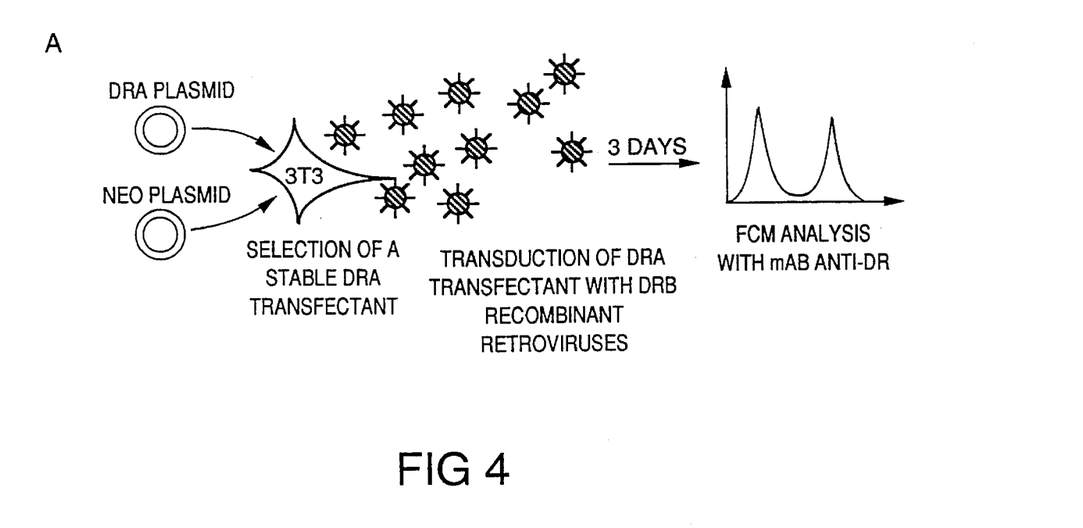
FIG. 4 is a diagram of the transduction assay.

The class II transduction assay was performed as diagramed in FIG. 4. NIH 3T3 cells were transfected with the SLA-DRA$^d$ cDNA inserted in a plasmid expression vector, Okayama et al., 1982, Mol. Cell. Biol. 2:161–170. Approximately 3×10$^4$ cells of a stable DRA transfectant (clone 11/12.2F) that expressed a high level of DRA mRNA were then transduced overnight with 1 ml of DRB-containing retroviral supernatant. Cells were subsequently cultivated in fresh DMEM supplemented with 10% fetal bovine serum and antibiotics for 2 additional days and examined for cell surface expression of the DR antigen by FCM analysis.

The class II transduction assay described here provides a fast and simple method to test both the expression and functional titer of retroviral constructs. By using cells transfected with DRA, the need for lengthy double selection after transduction by two separated vectors, Yang et al., 1987, Mol. Cell Biol. 7:3923–3928; Korman et al., 1987, Proc. Natl. Acad. Sci. USA 84:2150–2154, is obviated. Cell-surface expression of DR heterodimers was demonstrated by FCM analysis 3 days after transduction, providing direct evidence that the transferred sequences were sufficient to produce significant level of DR β chain. More importantly, this test allows determination of "functional" titers based on the expression of the gene of interest rather than on that of the independently regulated drug-resistance marker.

The SLA-DRB probe was an EcoRI cDNA fragment containing the complete coding sequence of the DR β chain, Gustafsson et al., 1990, Proc. Natl. Acad. Sci. USA 87:9798–9802. The neomycin phosphotransferase gene (Neo) probe was the Bcl I-Xho I fragment of the N2A retroviral plasmid, Hantzopoulos et al., 1989, Proc. Natl. Acad. Sci. USA 86:3519–3523.

Expression of Porcine DRB cDNA Transduced into Murine Bone Marrow Progenitor Cells The efficiency with which myeloid clonogenic precursors were transduced was determined by assaying for CFU-GM with and without a selecting amount of G418 after exposure of bone marrow cells to GS4.5-derived virions. Comparison of the number of colonies that formed in the presence and absence of the drug, for two experiments, indicated that ≈40% of the initial population of myeloid progenitor cells were transduced. The frequency of G418$^r$ CFU-GM was again determined after a sample of the transduced marrow was expanded under long-term culture conditions for 33 days. Twenty-five percent of the progenitors present after 33 days in culture still gave rise to colonies under G418 selection. Colonies of cells arisen from CFU-GM were examined for the presence of DRB-specific transcripts by converting RNA into cDNA and then performing PCR amplification as described herein and in Shafer et al., 1991 Proc. Natl. Acad. Sci. USA 88:9670. A 360-bp DRB-specific product was detected in five of six G418-selected colonies from freshly transduced marrow, whereas all six colonies similarly derived from transduced progenitors present after 33 days in culture were positive. An additional band of 100 bp observed in some of the samples probably reflects the stochastic nature of nonspecific priming events. DRB-specific transcripts were also detected in the bulk population of drug-resistant colonies and in producer cells but were not detected in controls such as a bulk population of untransduced colonies, fibroblasts used to provide carrier RNA, and a bulk population of transduced colonies processed as above but without reverse transcriptase. These latter data demonstrate that the PCR signal was dependent on the synthesis of cDNA, excluding the possibility that provirus, rather than viral message, was responsible for the amplified fragment.

Recent improvements including modifications of the virus design, increase of viral titers, use of growth factors to stimulate precursor cells, and selection of stem cells prior to transduction have been shown to improve long-term expression of transduced genes in the hematopoietic compartment, Bodine et al., 1990, Proc. Natl. Acad. Sci. USA 87:3738–3742; Bodine et al., 1989, Proc. Natl. Acad. Sci. USA 86:8897–8901; Wilson et al., 1990, Proc. Natl. Acad. Sci. USA 87:439–443; Kang et al., 1990, Proc. Natl. Acad. Sci. USA 87:9803–9807; Bender et al., 1989, Mol. Cell. Biol. 9:1426–1434. The experiments herein show the applicability of the retroviral gene-transfer technique in achieving expression of major histocompatibility complex class II genes transferred into hematopoietic cells. To determine the efficiency with which developmentally primitive hematopoietic cells were transduced, the frequency of G418$^r$ CFU-GM was assessed after expanding infected marrow cells kept for 33 days in long-term cultures. Expression of the exogenous DRB cDNA was also monitored in cells derived from transduced CFU-GM present either immediately after infection or after an extended culture period. Virtually all of the colonies individually tested were positive for DRB-specific transcript, suggesting that the DRB recombinant vector is suitable for expression in murine hematopoietic cells.

Bone marrow cells were obtained from the femora of 6- to 12-week-old female C57BL/10 mice and were prepared as described, Ildstad et al., 1984, Nature 307:168–170. Methylcellulose colony assays for granulocyte/macrophage colony-forming units (CFU-GM), Eaves et al., 1978, Blood 52:1196–1210, were performed as described using 5% (vol/vol) murine interleukin 3 culture supplement (Collaborative Research). Long-term Dexter-type bone marrow cultures were initiated in 60-mm culture dishes with 2×10$^7$ nucleated cells, Eaves et al., 1987, CRC Crit. Rev. Oncol. Hematol. 7:125–138.

Bone marrow cells were transduced essentially as described, Bodine et al., 1989, Proc. Natl. Acad. Sci. USA 86:8897–8901. Briefly, bone marrow was harvested for 6–12-week-old female C57BL/10 donors that had been treated 2 days with 5-fluorouracil (150 mg/kg). Prestimulation was performed by incubating 1×10$^6$ cells per ml for 2 days in long-term Dexter-type bone marrow culture medium to which was added 7.5% interleukin 3 culture supplement and recombinant human interleukin 6 (200 units/ml; gift from J. Jule, National Institutes of Health, Bethesda, Md.). Marrow cells were transduced for 48 hr by adding 5×10$^6$ cells per 10-cm plate containing nearly confluent virus-producers, Polybrene (8 mg/ml), and the cytokines described above.

Detection of DRB-Specific Transcripts in CFU-Derived Colonies was performed as follows. Cells corresponding to individual CFU colonies and to colonies present on an entire plate (bulk) were first extracted from methylcellulose cultures by dilution in phosphate-buffered saline and centrifugation. These cells were then combined with 1×10$^6$ NIH 3T3 cells (to provide carrier RNA), and total RNA was prepared using the guanidine isothiocyanate/CsCl method. First-strand cDNA was prepared from 20 µg of total RNA using the Invitrogen Red Module kit. cDNA was then subjected to 50 cycles of PCR amplification in the presence of the SLA DRB-specific oligonucleotides 04 (5'-CCACAGGCCT-GATCCCTAATGG) (Seq. I.D. No. 1) and 17 (5'-AGCAT-AGCAGGAGCCTTCTCATG) (Seq. I.D. No. 2) using the Cetus GeneAmp kit as recommended (Perkin-Elmer/Cetus). Reaction products were visualized after electrophoresis on a 3% NuSieve agarose gel (FMC) by staining with ethidium bromide.

FCM analysis was performed with a FAC-Scan II fluorescence-activated cell sorter (Becton Dickenson) on cells stained with the anti-DR monoclonal antibody 40D, Pierres et al., 1980, Eur. J. Immunol. 10:950–957, an anti-H-$2^d$ allo antiserum, or the anti-porcine CD8 monoclonal antibody 76-2-11, Pescovitz et al., 1984, J. Exp. Med. 160:1495–1505, followed by fluorescein isothiocyanate-labeled goat anti-mouse antibodies (Boehringer Mannheim).

EXAMPLE 2

Expression of Allogeneic Class II cDNA in Swine Bone Barrow Cells Transduced With A Recombinant Retrovirus A MHC gene (DRB) was transferred into clonogenic progenitor cells from swine using a recombinant retroviral vector (GS4.5) and a transduction protocol designed to be applicable in vivo. Both the selectable drug resistance gene and the allogeneic class II cDNA transferred by this vector were expressed in the progeny of these transduced progenitors. Expression of the Neogene was monitored functionally by colony formation under G418 selection, while the presence of class II transcripts was detected by PCR analysis. With this latter method, the transcriptional expression of both endogenous and virally derived DRB genes in transduced and selected colonies were demonstrated.

Primary porcine fibroblasts were cultured with high titer viral supernatants, and then analyzed by northern blotting using probes specific for DRB and Neo. A specific transcript was observed which was uniquely hybridizable with the DRB probe and migrated at the position predicted (1700 bases) for the DRB cDNA transcription unit arising from the TK promoter and terminating at the LTR 3' RNA processing site.

To determine whether GS4.5 containing virions could transduce swine myelopoietic progenitor cells a colony assay adapted for swine CFU-GM was used. Transductions were carried out by incubating bone marrow from a donor of the $SLA^c$ haplotype in high titer viral supernatant. Comparisons of the number of colonies which formed in the presence and absence of G418 for a total of 5 independent experiments indicated that 5% to 14% of CFU-GM were transduced.

Colonies of cells originating from transduced CFU-GM were examined for the presence of DRB-specific transcripts by converting RNA into cDNA, and then performing PCR amplification. Utilizing a polymorphic Sau3AI restriction site absent from the endogenous $DRB^c$ gene, the presence of $DRB^d$-specific transcripts was unambiguously demonstrated. Gel electrophoresis of the PCR product demonstrated that a 183/177 bp doublet indicative of the vector-derived $DRB^d$ transcript was amplified in samples derived not only from pools of transduced and selected CFU-GM progeny, but also from at least 4 out of 6 individual colonies tested. A 360 bp PCR fragment, indicative of endogenous $DRB^c$ transcripts, was also amplified not only as expected from PBL isolated from an $SLA^c$ donor, but also from both of the pooled colony samples and a number of the individual colony samples.

Construction of the retrovirus GS4.5, and production of high titer viral supernatants was as described above. Detection of DRB-specific transcripts in CFU-derived colonies by PCR of cDNA were described above and as follows. Bone marrow from an $SLA^c$ donor was exposed to GS4.5-containing virions, and G418 selected colonies were tested for the presence of $DRB^c$ (endogenous) and $DRB^d$ (vector derived) specific transcripts by PCR of cDNA followed by digestion with Sau3AI and agarose gel electrophoresis. Controls were as follows: template synthesized either in the presence or absence of reverse transcriptase; template derived from cells producing GS4.5-containing virions, from PBL isolated from $SLA^c$ or $SLA^d$ donors, and from untransduced producer cells used as carrier RNA.

Transduction of bone marrow was performed as follows. Swine bone marrow was harvested as previously described (Pennington et al., 1988, Transplantation 45:21–26) and transductions were carried out by incubating marrow cells in high titer viral supernatants at an m.o.i. of 3–5 in the presence of 8 ug of polybrene per ml at 37° C. for 5 hr. Myeloid progenitors were assayed by colony formation in methylcellulose cultures using PHA-stimulated swine lymphocyte conditioned medium as a source of growth factors. Selective medium contained 1.2 mg/ml active G418.

Transduced bone marrow was administered to a lethally irradiated miniature swine. At 5 weeks peripheral blood lymphocytes were analyzed by Southern, northern, and cell-surface FACS analyses. By all of these test there was evidence of presence of the transduced allogeneic class II gene in these cells and for expression of the product of this gene. In particular, northern analysis showed bands characteristic of the transcribed cDNA, and FACS analysis with a combination of alloantisera and monoclonal antibodies to DR showed presence of the transduced allele of DR beta on the surface of peripheral lymphocytes.

EXAMPLE 3

Allogenic Tolerance

Development of the B10.MBR—B10.AKM Strain Combination In an attempt to maintain strains which are truly congenic for the MHC, a program of continuous backcrossing of each congenic line to a common background partner strain was instituted more than 15 years ago. Backcross animals were intercrossed and appropriate progeny selected by serologic typing in order to reestablish each congenic line. Thus, C57BL/10 was used as one reference background strain and all other congenic lines on the B10 background were backcrossed once every six to ten generations to this C57BL/10 line.

Figure 5:
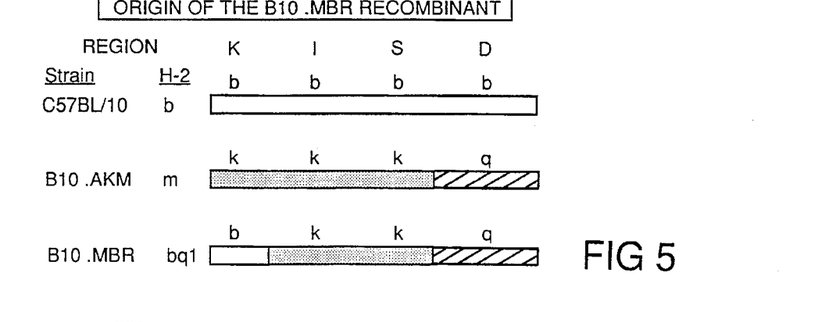
FIG. 5 is a diagram of genetic maps of the C57BL/10, B10.AKM, and B10.MBR strains.

During the backcrossing of each congenic line to its pedigreed reference line, there is of course the chance for an intra-MHC recombination event to occur. Typing of the intercross ($F_2$) generation serologically reveals such recombinant events, and when the recombinant provides a new haplotype of potential interest for genetic studies, it is outcrossed and then intercrossed to produce a homozygous new recombinant H-2 haplotype. One of the most valuable of such recombinants originating in this colony is the B10.MBR line, Sachs et al., 1979, J. Immunol. 123:1965–1969, which was derived from a recombination event during the backcrossing of B10.AKM to C57BL/10. Because this strain was the first to separate $K^b$ from $I^k$ it has been used extensively in studies of H-2 immunogenetics. In addition, in combination with the parental B10.AKM strain, the B10.MBR offers the possibility of examining an isolated K gene as the only MHC difference between these two strains. Thus, as illustrated in FIG. 5, introduction of the $K^b$ gene into B10.AKM bone marrow stem cells, could theoretically lead to expression of all cell surface MHC antigens of the B10.MBR. Expression on bone marrow derived cell populations produces transplantation tolerance to the product of the transduced gene, and this tolerance can be tested by a tissue graft from the B10.MBR strain.

Reconstitution of Myeloablated Mice with Transduced Bone Marrow Eighty prospective donor B10.AKM mice were treated with 150 mg/kg 5FU on day −7. Bone marrow was harvested from these mice on day −5, treated with anti-CD4 and anti-CD8 monoclonal antibodies (mAbs) plus complement to remove mature T cells, and cultured for five days with N2-B19-H2b virus-containing supernatant (H2) from the psi-Crip packaging cell line. As a control, one-half of the marrow was cultivated with supernatant from control packaging cells not containing N2-B19-H2b (A2). On day zero, 45 B10.AKM recipients received 10 Gy total body irradiation (TBI), followed by administration of various concentrations of cultured bone marrow cells (A2 or H2).

Figure 6:
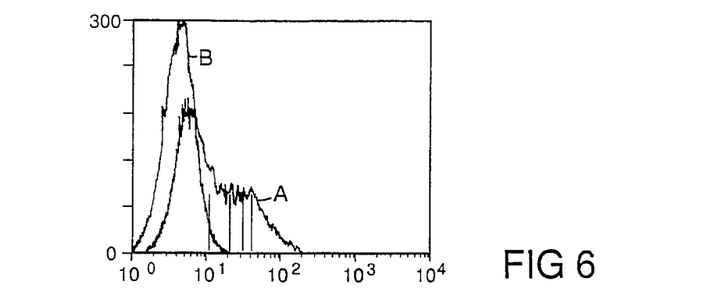
FIG. 6 is a diagram of the FACS profile of spleen cells from a recipient of transduced bone marrow.

$K^b$ expression On day 13 several animals receiving the lowest doses of cultured bone marrow were sacrificed and individual spleen colonies were harvested and analyzed by PCR for the presence of N2-B19-H2b DNA. In addition, spleen cell suspensions were prepared and analyzed for cell surface expression of $K^b$ by flow microfluorometry on a fluorescence-activated cell sorter (FACS). FACS analyses indicated that all animals receiving the H2-treated marrow showed some level of $K^b$ expression above control staining with the non-reactive antibody. The results are shown in FIG. 6 which is a FACS profile of spleen cells from a recipient of transduced bone marrow: A=Anti $K^b$ antibody; B=control antibody. Spleen cells from recipients of non-transduced marrow were also negative. In addition, the PCR analysis showed every colony examined to contain the transduced DNA. Animals were thereafter followed by FACS and PCR on peripheral blood lymphocytes (PBL). On day 28 and again on day 40, PCR analyses were positive. However, FACS analysis for cell-surface expression was variable, with PBL from most H2 animals showing only a slight shift of the entire peak for staining with anti-$K^b$, as compared to PBL from A2 animals stained with the same antibody, or as compared to PBL from H2 animals stained with the non-reactive HOPC antibody.

Figure 7A:
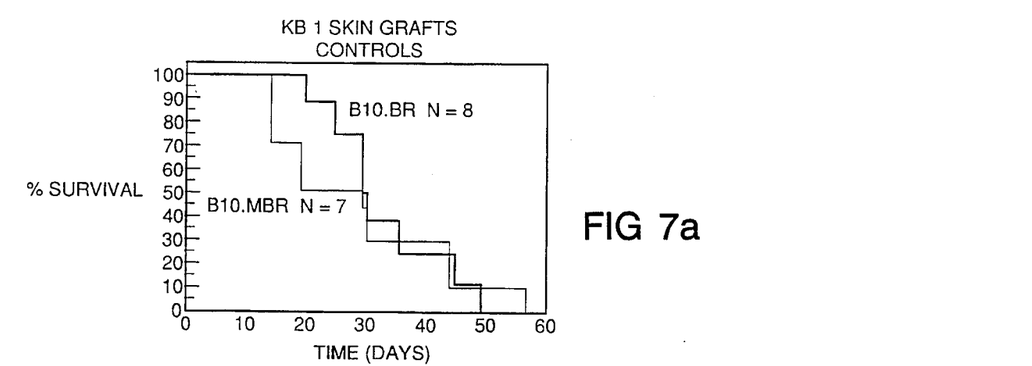
FIG. 7 is a graph of survival versus time in skin graft experiments.
Figure 7B:
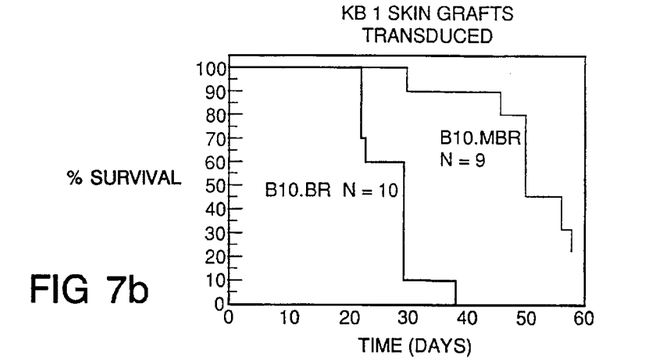
Figure 8A:
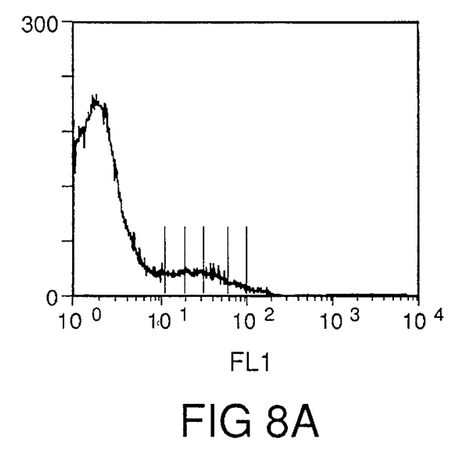
FIG. 8 is a diagram of FACS analysis of thymocytes from graft rejectors, receptors, and controls.
Figure 8B:
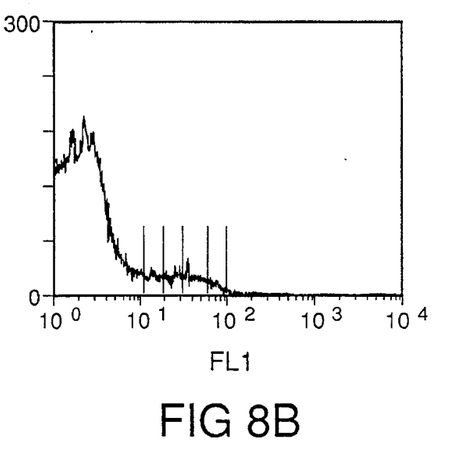
Figure 8C:
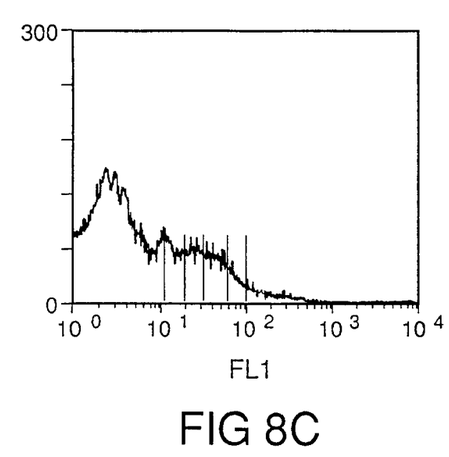
Figure 8D:
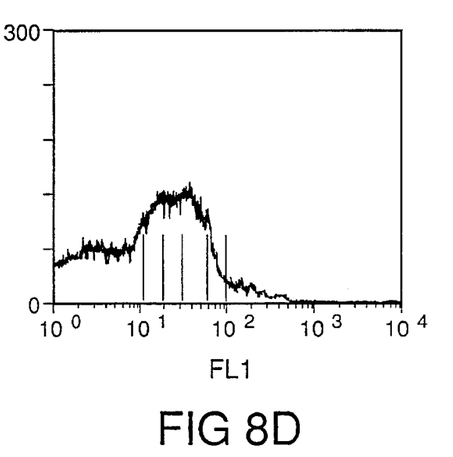

Allogeneic grafts On day 40 skin from B10.MBR ($K^b$ specific) and B10.BR (control, third party class I disparate) donors was grafted onto all animals. Graft survivals were scored daily by a blinded observer (i.e., readings were made without knowledge of which graft was from which donor strain) until rejection was complete. The survival times are shown in FIG. 7, and indicate marked specific prolongation of survival of the B10.MBR skin grafts on the recipients of $K^b$-transduced BMC (FIG. 7B), but not on recipients of control marrow (FIG. 7A). One of the animals with a long-standing intact B10.MBR skin graft was sacrificed at day 114 and cell suspensions of its lymphoid tissues were examined by FACS and compared to similar suspensions of cells from an animals which had rejected its B10.MBR skin graft. A striking difference was noted in staining of thymus cells with an anti-$K^b$ mAb. Cell suspensions were prepared and stained either with the anti-$K^b$ mAb 28-8-6 or the control antibody HOPCl. A subpopulation of thymus cells from the tolerant animal showed a marked shift toward increased staining with 28-8-6 compared to HOPCl, while there was essentially no change in the staining pattern of thymocytes from the animal which had lost its graft. FIG. 8 shows FACS analysis on thymocytes from skin graft rejector (FIGS. 8A, B) and skin graft acceptor (FIGS. 8C, D). Staining with control HOPCl antibody (FIGS. 8A, C) and with specific anti-$K^b$ antibody (FIGS. 8B, D). A similar comparison of staining patterns on bone marrow cells showed the presence of low level $K^b$ expression on a cell population in the marrow of the tolerant mouse, but not of the mouse which had rejected its skin graft. These results indicate that a pluripotent stem cell or early progenitor cell population expressed $K^b$ in the tolerant mouse but not in the rejector mouse, and that this BMC stem cell provided a continuous source of $K^b$ antigen in the thymus on cells which are critical for the inactivation of developing thymocytes with $K^b$-reactive TCR. It is of interest to note that $K^b$ expression was not detected on splenocytes of the tolerant mouse, and that, in general, splenocyte expression did not correlate with skin graft tolerance. Since the spleen contains T cells which mature in the thymus, these results suggest that either thymocytes lose expression of $K^b$ as they mature, or that the $K^b$-bearing thymocytes of this animal were cells of a non-lymphoid lineage, such as macrophages.

Long-term expression As discussed above, the B10.AKM and B10.MBR congenic mouse strains are identical except in the MHC class I region. A recombinant retrovirus containing the class I gene from the B10.MBR stain (H-2$K^b$) linked to a B19 parvovirus promoter (B19-H2$K^b$) and a neomycin resistance (neo$^r$) gene was introduced into B10.AKM (H-2$K^k$) marrow cells. As a control, a recombinant retrovirus containing only the neo$^r$ gene was introduced into B10.AKM marrow cells. The transduced marrow was injected into lethally irradiated AKM recipients pre-treated with an anti-CD8 monoclonal antibody. Twelve weeks post BMT, quantitative PCR was used to show that the B19-H-2$K^b$proviral sequences were present in 5%–30% of peripheral blood cells in all recipient animals. Reverse transcriptase PCR was used to demonstrate the B19-H-2$K^b$ mRNA in RNA isolated from bone marrow and spleen of a subset of recipient animals.

Figure 9:
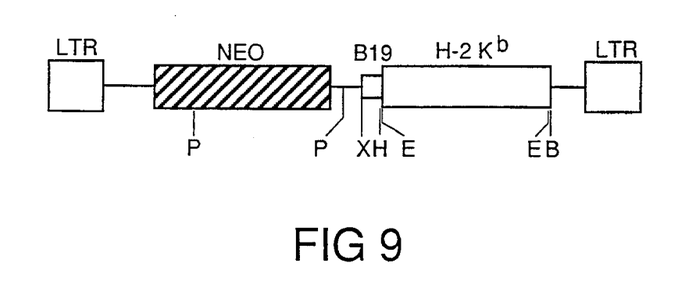
FIG. 9 is a diagram of the N2-B19-H2b vector.

Construction of the $K^b$ Retroviral Vector The retroviral vectors used the Maloney murine leukemia virus based vector N2, Armentano et al., 1987, J. Virol. 61:1647–1650. The coding regions within this virus were deleted during its construction, and replaced with the selectable marker gene, neomycin phosphotransferase (Neo), which is transcribed from the viral LTR promoter, and provides drug resistance to G418. This conventional N2 virus was then further modified by insertion of a parvovirus-derived promoter, B19, Liu et al., 1991, J. Virol. (In Press), downstream from Neo, followed by 1.6 kb of cDNA coding for the class I antigen H-2$K^b$ to form the new recombinant virus N2-B19-H2b. FIG. 9 depicts the N2-B19-H26 retroviral vector: P=PstI; X=XhoI; H=HinDIII; E=EcoRI; B=BamHI. This latter cDNA was derived by Waneck et al. during the construction of an H-2$^b$ cDNA library for other purposes, Waneck et al., 1987, J. Exp. Med. 165:1358–1370.

Viral producer cell lines were developed using the packaging cell lines for amphotropic (psi-Crip), Danos et al., 1988, Proc. Natl. Acad. Sci. 85:6460–6464, and ecotropic (psi-2), Sambrook et al., 1989, Molecular cloning: A laboratory manual. Cold Spring Harbor Laboratory Press, Cold Spring Harbor, viral production. These cell lines have been specially designed to produce structural viral proteins for the recombinant defective virus to be produced. Viral production was achieved by transfecting psi-Crip with N2-B19-H2b. Both amphotropic and ecotropic producer cell lines were then co-cultivated allowing multiple integration events and high expression [i.e. the "ping-pong" technique see Bestwick et al., 1988, Proc. Natl. Acad. Sci. 85:5404–5408]. In this technique, co-cultivation overcomes viral antigen receptor blockage by endogenously secreted proteins since amphotropic and ecotropic viruses recognize different receptors. Ecotropic psi-2 viral producer clones were then selected which produced titers of G418 resistance on 3T3 cells of greater than $10^7$ cfu/ml.

In order to ensure that $K^b$ was being expressed from the recombinant virus, transduced 3T3 cells were stained with a monoclonal antibody specific to this antigen and analyzed by flow microfluorometry. These experiments clearly demonstrated high level expression of virally derived $K^b$.

Animals and husbandry were as follows. The B10.BMR strain, [Sachs et al., 1979, J. Immunol. 123:1965–1969, was provided to the Jackson Laboratory, Bar Harbor, Me. about 6 years ago, and specific pathogen-free stock animals of this strain are now available from that source. Upon arrival in animals should be transferred to autoclaved microisolator cages containing autoclaved feed and autoclaved acidified drinking water. Sterile animal handling procedures which are effective in maintaining animals free of pathogens so that interpretable survival studies can be performed should be used.

Bone marrow transplantation was performed as follows. Techniques for bone marrow transplantation in mice are known to those skilled in the art, see e.g., Sykes et al., 1988, J. Immunol. 140:2903–2911. Briefly, recipient B10.AKM mice aged 12 to 16 weeks are lethally irradiated (1025R, 137Cs source, 110R/min) and reconstituted within 8 hours with $2.5 \times 10^6$ bone marrow cells, obtained from the tibiae and femora of sex-matched donors aged 6–14 weeks. Animals are housed in sterilized microisolator cages, and receive autoclaved food and autoclaved acidified drinking water. For these studies some modifications of this general technique are required, since the syngeneic bone marrow will have been transduced with an allogeneic gene, and since the bone marrow will come from 5FU-treated mice, which should have lower total cell counts but higher stem cell content than normal mice. The protocol is therefore as follows:

1. Donors will be treated with 5-Fluorouracil, 150 mg/kg i.v. on day −7 in order to induce pluripotent stem cells to cycle.

2. Marrow will be harvested from donors on day −5, and T cell depleted with mAbs and complement.

3. Marrow will than be cultured for 5 days in supernatant from an ecotropic packaging cell line (B17H2Kb-18) which produces a high titer of non-infectious retroviral particles containing the $K^b$ gene (see below). IL-3 and IL-6 will be added to the cultures.

4. On day 0, recipient B10.AKM mice will be lethally irradiated (10.25 Gy), and will be reconstituted with $2.5 \times 10^6$ BMC transduced with the $K^b$ gene. Control animals will be similarly treated, except that they will receive marrow exposed to supernatant from a similar ecotropic packaging line not exposed to a $K^b$-containing vector. The recipient may also be pre-treated with anti-CD8 monoclonal antibody.

Cellular and serological assays are performed as follows.

Anti-class I Cell-Mediated Lympholysis (CML) Assay: Spleens are removed from BMT recipients and normal mice, red cells are lysed using ACK buffer, and a single cell suspension is prepared. Cells are filtered through 100-mesh nylon, washed, and resuspended at $4 \times 10^6$/ml in complete medium consisting of RPMI 1640 with 10% fetal calf serum, 0.025 mM 2-mercapteothanol, 0.01M Hepes buffer, 0.09 mM nonessential amino acids, 1 mM sodium pyruvate, 2 mM glutamine, 100 U/ml penicillin and 100 ug/ml streptomycin. 90 μl of responder cells are added to Costar 96-well round-bottomed plates along with irradiated (30 Gy) stimulator splenocytes. Cultures are set up in two rows of 3 replicates each, and after 5 days of incubation in 6% $CO_2$ at 37° C., twofold serial dilutions are prepared from the second row of triplicates, so that cytolytic capacity can be examined at a total of 5 different responder:target ratios. $^{51}$Cr-labelled 2-day concanavalin A-induced lymphoblasts are then added at $10^4$ blasts per well and incubated for 4 hr at 37° C., 6% $CO_2$. Plates are harvested using the Titertek supernatant collection system (Skatron, Inc., Sterling, Va.) and $^{51}$Cr release is determined using an automated gamma counter. Cytolytic capacity is measured directly in the original cell culture plated, so that the measurement is based on the number of responders plated, rather than on the number of live cells present a the end of the 5-day incubation period. This methodology has been developed and used successfully in this laboratory for several years for analysis of spleen cell responses from individual animals [Sykes, M., et al., 1988 J.Immunol. 140:2903–2911]. Percent specific lysis is calculated using the formula:

$$\% \text{ Specific Lysis} = \frac{\text{Experimental release} - \text{Spontaneous release}}{\text{Maximum release} - \text{Spontaneous release}} \times 100\%$$

Limiting dilution analyses: Responder and stimulator ($6 \times 10^5$, 30 Gy irradiated) cells are concultured for 7 days in complete medium containing 13% TCGF (lectinin-activated con A supernatant obtained from BALB/c con A-activated splenocytes) in 96-well plates. Wells containing $10^5$ (24 wells), $3 \times 10^4$ (24 wells), $10^4$ (30 wells), 3000 (30 wells), 1000 (30 wells), 300 (30 wells), and 100 (30 wells) responder cells are prepared. Three thousand $^{51}$Cr-labelled con A blasts are added to each well on day 7, and 4 hour $^{51}$Cr release is measured. Wells are considered positive if $^{51}$Cr release is 3 standard deviations greater than the mean $^{51}$Cr release in 24 wells containing stimulator cells only plus similar numbers of target cells. The Poisson distribution is used to determine the frequency of precursor CTL's which recognize each target, and statistical analysis is performed by the Chi square method of Taswell, Taswell, 1981, J.Immunol. 126:1614.

Flow microfluorometry: One-color and two-color flow cytometry will be performed, and percentages of cells expressing a particular phenotype will be determined from 2-color data, as previously described in detail Sykes, 1990, J.Immunol. 145:3209–3215. The Lysis II software program (Becton Dickinson) will be used for distinguishing granulocytes from lymphocytes by gating on the basis of forward angle and 90° light scatter. Cell sorting will be performed on a Coulter Epics Elite cell sorter. Cell suspensions for flow cytometry: PBL, BMC, thymocyte, splenocyte, and lymph node suspensions will be prepared as previously described, Sykes, M. et al., 1988, J.Immunol. 140:2903–2911; Sykes, M. 1990, J.Immunol. 145:3209–3215; Sharabi, Y. et al., 1990, J.Exp. Med. 172:195–202 Whole peripheral white blood cell suspensions (including granulocytes) will be prepared by centrifugation of heparinized blood for 2 minutes at 14,000 RPM in an Eppendorf centrifuge, followed by aspiration ob the buffy coat layer. These cells will be transferred to a 15 ml. conical tube and washed. Red blood cells (RBC) contaminating the remaining pellet will be lysed by exposure for 5 seconds to 4.5 ml of distilled $H_2O$ followed by rescue with 0.5 ml of 10×PBS.

Cell staining: One-color and two-color staining will be performed as we have previously described, Sykes, M., 1990, J. Immunol. 145:3209–3215; Sykes et al., 1988, J. Immunol. 141:2282–2288. Culture supernatant of rat anti-mouse RcτR mAB 2.4G2, Unkeless, J. C., 1979, J. Exp. Med. 150:580–596, will be used for blocking of non-specific staining due to FcτR binding, whenever only direct staining is used. The following mABs are sued: biotinylated murine $K^b$-specific $IgG_{2a}$ mAB 28-8-6, Ozato et al., 1981, J. Immunol. 126:317–321, and control murine $IgG_{2a}$ mAB HOPC1 (with no known specific binding to murine antigens) are prepared by purification on a protein A-Sepharose column, and are biotinylated by standard procedures used in our laboratory; rat anti-MACl mAB M1/70, Springer et al, 1979, Eur. J. Immunol. 9:301, is used as culture supernatant, and will be stained by mouse anti-rat IgG-specific mAB MAR18.5; FITC-labelled rat-anti-mouse granulocyte antibody Gr1 is purchased from Pharmingen; FITC-labelled rat-anti-mouse IgM mAb is purchased from Zymed; FITC-labelled rat-anti-mouse Thy1.2 mAb will be purchased from Becton-Dickinson; FITC-labelled mouse-anti-human CD3 mAb Leu4 (Becton Dickenson) is used as a directly FITC labelled negative control antibody.

Thymic tissue immunofluorescence: The tissue is incubated in L15 medium for 24 hours to reduce background staining, and is then cut and embedded in O.C.T. compound for freezing in Isopentane. Frozen sections are prepared (thickness 4 μm) on a cryostat, dried, fixed in acetone, then washed in PBS. The first antibody incubation (with 28-8-6) is performed in the presence of 2% normal mouse serum, in order to saturate Fc receptors. After 45 minutes, the slides are washed 4 times, and FITC-conjugated secondary reagent (monoclonal rat-anti-mouse IgG2a-FITC, purchased from Pandex) is added. After 45 minutes' incubation with the secondary reagent, four washes are performed and the tissue is mounted. Sections are examined under a fluorescence microscope by an observer who is unaware of the group of animals from which the tissue was obtained.

Bone Marrow Manipulations and Assays were performed as follows:

Transduction of murine bone marrow stem cells: The methodology used for transduction of bone marrow cells has been described previously, Karlsson et al., 1988, Proc. Natl. Acad. Sci. 85:6062–6066. Bone marrow is harvested from 6–12 week old female B10.AKM donors treated 2 days previously with 150 mg/kg 5-FU. Following T cell depletion (see above), the marrow is divided and $10^7$ cells per 10 cm plate are cultured for 5 days in the presence of 8 μg of Polybrene per ml, 10% FCS, 0.6% IL-3-containing supernatant, 0.6% IL-6-containing supernatant, and fresh supernatants from B19H2$K^b$ or N2 cells. IL-3- and IL-6-containing supernatant is 48 hour supernatant of COS 7 cells transfected with the murine rIL-3 gene-containing plasmid pCD-IL-3 or with the murine rIL-6 gene-containing plasmid pCD-IL-6, respectively (both plasmids provided by Dr. Frank Lee, DNAX Corp.). IL-3-containing supernatants are tittered by testing proliferation of the IL-3-dependent cell line 32D in the presence of dilutions of these supernatants, and IL-6 is tittered in a similar manner using the IL-6-dependent line T1165 as the indicator cell line. We will also test the effect of murine SCF on bone marrow transduction, as recently described, Zsebo et al., 1990, Cell 63:125–201.

The virus-containing supernatants are refreshed on a daily basis by harvesting the non-adherent layer of each plate, pelleting the cells, and resuspending in freshly harvested filtered virus-containing B19H2$K^b$ or N2 supernatant with additives. After 5 days, the non-adherent and adherent BMC are harvested, washed, and resuspended at $2.5 \times 10^6$/ml in Medium 199 with Hepes buffer and Gentamycin plus Heparin 10 U/Ml. One ml. of this suspension is injected i.v. to irradiated mice.

Murine CFU-GM assay: To test for the bone marrow progenitor cells known as CFU-GM (colony forming unit-granulocyte/macrophage), bone marrow cells are suspended in plating medium consisting of IMDM medium containing 30% defined fetal bovine serum (FBS) (HyClone, Logan, Utah), $10^{-4}$M β-mercaptoethanol, antibiotics, 5% v/v murine IL-3 culture supplement (Collaborative Research Inc., Bedford, Mass.) and 0.8% methylcellulose (achieved by adding 36% v/v of a commercially prepared solution purchased from the Terry Fox Laboratory, Vancouver). 1.1 ml of this suspension is then dispensed into 35 mm tissue culture plates (in duplicate), and placed in a 37° C. incubator. The resulting CFU-GM derived colonies are enumerated microscopically after 5–7 days. Transduced CFU-GM are selected by including 0.9 ug/ml active G418 in the culture medium. The transduction frequency is then determined by the ratio of CFU-GM which form colonies in the presence and in the absence of the drug.

Molecular methods were as follows:

Construction of N2-B19-H2b vector: This vector was constructed staring from the original retroviral vector N2, Eglitis et al., 1985, Science 230:1395–1398, as modified by Shimada to include an additional BamHI site immediately 3' of the XhoI site. It includes the $K^b$ cDNA previously cloned in the vector pBG367, as described by G. Waneck, Waneck et al., 1987, J. Exp. Med. 165:1358–1370. This gene has been placed under control of the B19 promoter, a highly efficient parvo virus derived promoter, Liu et al., 1991, J. Virol. In Press:] to produce the N2-B19-H2b construct.

Southern blot analysis can be performed on DNA extracted from PBL, thymocyte, BMC, splenocyte or lymph node cell suspensions using standard methods, Ausubel et al., 1989, Current protocols in molecular biology. John Wiley & Sons, New York, and probing will be performed with the fragment of $K^b$ cDNA released from pBG367 by EcoRI. The genomic DNA will be cut with enzymes capable of distinguishing the transduced $K^b$ from other class I genes of the B10.AKM strain. From known sequences it would appear that EcoRI may be satisfactory for this purpose, since it should liberate a 1.6 kb band from the transduced $K^b$ cDNA, which is distinct from both the expected endogenous $K^k$ and $D^q$ class I bands of B10.AKM, Arnold et al., 1984, Nucl. Acids Res. 12:9473–9485; Lee et al., J. Exp. Med. 168:1719–1739. However, to assure that there is no confusion with bands liberated from other class I and class I-like genes we will test several enzymes first on DNA from B10.AKM and choose appropriate restriction enzyme combinations.

PCR analysis of DNA can be performed using primers previously shown to be effective in our preliminary studies (see FIG. 4):

5' primer: 5'-GGCCCACACTCGCTGAGGTATTTCGTC-3' (covers 5' end of α1 exon) (Seq. ID No. 3)

3' primer: 5'-GCCAGAGATCACCTGAATAGTGTGA-3' (covers 5' end of α2 exon) (Seq. ID No. 4)

DNA is subjected to 25 cycles of PCR amplification using these specific oligonucleotides and the Cetus GeneAmp kit (Perkin Elmer Cetus, Norwalk, Conn.) according to the manufacturer's directions. In addition, $^{[32]}$PdCTP will be included in the PCR reaction in order to visualize products by autoradiography following electrophoresis.

RNA can be isolated from $5 \times 10^6$ to $5 \times 10^7$ cells using the guanidine isothiocyanate and CsCl methods, Chirgwin et al., 1979, Biochem. 18:5294–5308, and will be used for northern analyses, RNase protection analyses, and for PCR analyses of products formed by reverse transcriptase. For situations in which less then $5 \times 10^6$ cells are available, for example following tail bleedings of individual mice, we will utilize the QuickPrep mRNA Purification Kit (Amgen) as a miniaturized RNA preparation procedure.

Northern analyses can be carried out using standard methods, Ausubel et al., 1989, Current protocols in molecular biology John Wiley & Sons, New York, and the same $K^b$ cDNA-derived probe. Vector-derived $K^b$ mRNA is larger than endogenous class I transcripts (2.5 kb vs. 1.6 kb) due to the inclusion of vector sequences between the 3' end of the cDNA and the poly-adenylation site in the viral 3' LTR. It should therefore be easy to distinguish the vector-derive $K^b$ mRNA from endogenous transcripts that might cross-hybridize with a $K^b$ cDNA probe. We will also utilize probes derived from unique non-$K^b$ sequences of the transcript (e.g., from B19 or N2 derived vector sequences).

RNAse protection analyses are more sensitive than standard northern blots, yet still quantitative. Procedures based on published methods, Sambrook et al., 1989, Molecular cloning: A laboratory manual. Cold Spring Harbor Laboratory Press, Cold Spring Harbor, will be used to derive riboprobes. Briefly, the $K^b$ cDNA will be cloned into a plasmid vector containing the T3 and T7 RNA polymerase promoter sequences (bluescript or Bluescribe plasmids from Stratagene). Using appropriate polymerase and $^{32}P$-nucleotides, transcription of the insert will be initiated and the radioactive $K^b$ RNA will be purified. This probe will then be incubated with various RNA preparations followed by treatment with ribonuclease. Presence of RNA will be assessed by electrophoresis on a sequencing gel.

PCR following reverse transcriptase treatment of RNA will be used as a highly sensitive procedure for detecting the $K^b$ transcript. Appropriate primers will be designed in order to specifically amplify retroviral derived transcripts (one primer covering the 5'UT region of the construct and a second derived from the cDNA sequence). Briefly, RNA will be prepared by the GuSCN/CsCl method and first strand cDNA will be prepared from 5 ug of total RNA using the SuperScript preamplification system (BRL/Life Technologies, Inc., Gaithersburg, Md.). PCR amplifications will be conducted for 50 cycles, Hansen et al., J. Immunol. 118:1403–1408, using the Cetus GeneAmp kit (Perkin Elmer Cetus, Norwalk, Conn.). Reaction products will be visualized following electrophoresis on a 3% NuSieve agarose gel (FMC BioProducts, Rockland, Me.).

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear     ( x i ) SEQUENCE DESCRIPTION: SEQ ID NO: 1:

CCACAGGCCT GATCCCTAAT GG        22

( 2 ) INFORMATION FOR SEQ ID NO: 2:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear     ( x i ) SEQUENCE DESCRIPTION: SEQ ID NO: 2:

AGCATAGCAG GAGCCTTCTC ATG        23

( 2 ) INFORMATION FOR SEQ ID NO: 3:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear     ( x i ) SEQUENCE DESCRIPTION: SEQ ID NO: 3:

GGCCCACACT CGCTGAGGTA TTTCGTC        27

( 2 ) INFORMATION FOR SEQ ID NO: 4:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear     ( x i ) SEQUENCE DESCRIPTION: SEQ ID NO: 4:

GCCAGAGATC ACCTGAATAG TGTGA        25

Other embodiments are within the following claims.

What is claimed is:

1. A method for inhibiting a mammalian recipient's ability to mount an immune response against an MHC class II antigen of tissue from a donor mammal of the same species to be provided to a said recipient, comprising:

providing said recipient with a cell composition comprising recipient species bone marrow hematopoietic stem cells having inserted therein DNA encoding an MHC class II antigen to be expressed in said recipient, said MHC class II antigen being the same as that expressed by donor tissue to be provided to said recipient, to thereby inhibit said recipient's ability to mount an immune response against said MHC class II antigen expressed by the swine tissue.

2. A method for inhibiting a human recipient's ability to mount an immune response against an SLA class II antigen of swine tissue to be provided to a human, comprising:

providing a human recipient with a cell composition comprising human bone marrow hematopoietic stem cells having inserted therein DNA encoding a swine SLA class II antigen to be expressed in said human, said SLA class II antigen being the same as that expressed by swine tissue to be provided to said human, to thereby inhibit said human's ability to mount an immune response against the SLA class II antigen expressed by the swine tissue.

3. The method of claim 2, wherein said cell composition is removed from said recipient prior to said insertion and returned to said recipient after said insertion.

4. The method of claim 2, wherein said swine is a miniature swine.

5. The method of claim 2, wherein said DNA is obtained from the swine from which said tissue is obtained.

6. The method of claim 2, wherein said DNA is obtained from a swine which is syngeneic to the individual swine from which said tissue is obtained.

7. The method of claim 2, wherein said DNA is obtained from a swine which is SLA identical to the individual swine from which said tissue is obtained.

8. The method of claim 2, wherein said DNA is inserted into said cell by transduction.

9. The method of claim 8, wherein said DNA is inserted into said cell by a retrovirus.

10. The method of claim 9, wherein said retrovirus is a Moloney-based retrovirus.

11. The method of claim 1, wherein said cells are removed from said recipient prior to said insertion and returned to said recipient after said insertion.

12. The method of claim 1, wherein said recipient is a human.

13. The method of claim 1, wherein said DNA is inserted into said cells by transduction.

14. The method of claim 1, wherein said DNA is inserted into said cells by a retrovirus.

15. The method of claim 1, wherein said retrovirus is a Moloney-based retrovirus.

* * * * *

UNITED STATES PATENT AND TRADEMARK OFFICE
CERTIFICATE OF CORRECTION

PATENT NO.    : 5,614,187                                       Page 1 of 1
DATED         : March 25, 1997
INVENTOR(S)   : David H. Sachs It is certified that error appears in the above-identified patent and that said Letters Patent is hereby corrected as shown below:

<u>Column 21,</u>
Line 15, replace the word "swine" by -- donor --.

Signed and Sealed this

Twenty-fourth Day of December, 2002

JAMES E. ROGAN
*Director of the United States Patent and Trademark Office*